United States Patent [19]

Chace et al.

[11] Patent Number: 5,416,322
[45] Date of Patent: May 16, 1995

[54] INTERFACE FOR LINKING AN ATMOSPHERIC PRESSURE THERMOGRAVIMETRIC ANALYZER TO A LOW PRESSURE MASS SPECTROMETER

[75] Inventors: Mark S. Chace; Timothy J. MacMahon, both of Poughkeepsie, N.Y.

[73] Assignee: International Business Machines Corporation, Armonk, N.Y.

[21] Appl. No.: 230,984

[22] Filed: Apr. 21, 1994

[51] Int. Cl.⁶ .......................................... H01J 49/04
[52] U.S. Cl. ..................................... 250/288; 250/281
[58] Field of Search ........................ 250/288, 281, 282

[56] References Cited

U.S. PATENT DOCUMENTS

| | | | |
|---|---|---|---|
| 4,075,475 | 2/1978 | Risby et al. | 250/282 |
| 4,122,343 | 10/1978 | Risby et al. | 250/288 |
| 4,662,914 | 5/1987 | Hansen et al. | 55/386 |
| 4,982,097 | 1/1991 | Silvon et al. | 250/288 M |
| 4,985,625 | 1/1991 | Hurst | 250/288 |
| 5,122,670 | 6/1992 | Mylchreest et al. | 250/423 R |
| 5,162,650 | 11/1992 | Bier | 250/288 |
| 5,170,053 | 12/1992 | Hail et al. | 250/288 |
| 5,191,211 | 3/1993 | Gorman | 250/282 |
| 5,236,593 | 8/1993 | Cortes et al. | 210/656 |

OTHER PUBLICATIONS

M. S. Chace, "An Apparatus for Evolved Gas Analysis: Linking a Thermogravimetric Analyzer to an Ion Tray Detector (ITD)".
Finnigan MAT., Finnigan Corp., San Jose, Calif., Booklet, No. 218, 1988.
E. L. Charsley, et al., "Thermogravimetry-mass spectrometry using a simple capillary interface", American Laboratory, Booklet, Jan., 1990.

Primary Examiner—Jack I. Berman
Attorney, Agent, or Firm—H. Daniel Schnurmann

[57] ABSTRACT

An interface linking a mass spectrometer (MS) to a thermogravitational analyzer (TGA) for adjusting the concentration of volatiles entering the MS. The interface is preferably a capillary column provided with a dilution chamber having a inlet for gas insertion, with one end of the chamber connected to the TGA and the other to the capillary column having its other end directly attached to the MS. In a second embodiment, the interface bypasses the dilution chamber, and is made of a glass tubing protected by a stainless steel tubing, in turn surrounded by a temperature programmable sheath heater.

16 Claims, 4 Drawing Sheets

INTERFACE FOR LINKING AN ATMOSPHERIC PRESSURE THERMOGRAVIMETRIC ANALYZER TO A LOW PRESSURE MASS SPECTROMETER

FIELD OF THE INVENTION

This invention relates generally to mass spectrometers (MS) and thermogravimetric analyzers (TGA), and more particularly to an interface that allows the transfer of volatile species from an atmospheric pressure TGA to an evacuated MS analysis chamber.

BACKGROUND OF THE INVENTION

The basic function of a Thermogravimetric Analyzer (TGA) is to measure the amount and rate of weight change of a material, either as a function of increasing temperature, or isothermally as a function of time. During heating of a sample in a TGA, the sample may undergo changes that liberate gases. The TGA can interface with other analytical instruments (such as a gas chromatograph or mass spectrometer) for additional characterization of the evolved gases.

The basic purpose of a mass spectrometer (MS) is to convert a sample into products that are indicative of the original molecule. Vaporized sample molecules from a variety of possible inletting systems (typically a gas chromatograph or direct inlet probe) enter the source of the MS and interact with a beam of electrons to form a variety of products, including positive ions. This ion beam from the source is separated according to the respective masses of the ions by a variety of techniques, the two most common of which are magnetic deflection and quadropole filter. The masses and their relative abundances are displayed in a mass spectrum.

The mass spectra produced from individual compounds are a qualitative identification tool, and can be combined with other physical data for a compound to quantitatively characterize it.

Traditionally, mass spectrometers (MS) have also been used to act as detectors for gas chromatographs (GC). Moreover, the interface of a GC to an MS allows for the transfer of volatile species from a pressurized GC capillary column to an evacuated MS analysis chamber. Such an interface typically employs a transfer line which internally contains a splitting area wherein the pressure differential is equalized. In such a configuration, the ends of two capillary columns are brought into close proximity of each other, and samples from the pressurized GC column are swept by the inert gas flow into an evacuated capillary feeding into the MS. With a proper design, a MS can alternatively be used as a detector for a thermogravimetric analyzer (TGA). A GC-MS interface cannot function in a TGA-MS configuration for two reasons: 1) there is no capillary action from the TGA to deposit effluents in close proximity of the capillary column, and 2) there is no "head pressure" as exists with a GC to push concentrated effluents into the internal splitting area. As a result, insufficient quantities of volatiles make it into the MS.

Unlike the GC-MS configuration, wherein effluents remain under pressure, a TGA-MS combination allows for a sample to be outgassed at ambient pressure. This makes the TGA-MS combination particularly useful for understanding the behavior of compounds during conventional thermal processing. Additionally, it also allows for the identification of compounds that evolve during different stages of decomposition. These techniques have been successfully used in studies that range from thermal degradation of polymers to the analysis of sample contaminants.

The coupling of a MS to a TGA is particularly useful for understanding the real time behavior of the compounds at high temperatures. First, the detection in the MS occurs simultaneously as thermal reactions take place in the TGA. This allows for the identification of species that evolve at different temperatures and their correlation to the several weight loss regions. Secondly, the sample undergoing thermal decomposition in the TGA takes place at atmospheric pressure. This is a departure from conventional MS systems, wherein samples are typically introduced into the instrument via a solids introducing probe. Hence, the sample is vaporized in the vacuum. In contradistinction with the TGA used as the sample introduction system, vaporization of the sample occurs outside the MS at atmospheric pressure prior to its being drawn into the MS where ionization in vacuum takes place.

There are two major obstacles to overcome in interfacing a MS to a TGA. The first is the large pressure differential between the operating states of the two instruments. The low pressure (ranging from $10E-5$ to $10E-8$ torr) required for ionization and mass analysis in the MS is provided by a vacuum system, typically a turbomolecular or diffusion pumping system. The TGA, on the other hand, operates at atmospheric pressure. Any interface which couples the two systems must somehow compensate for this severe pressure differential.

The second obstacle to interfacing a MS to a TGA is the large mismatch in sensitivity between the TGA and the MS (MS being more sensitive to changes in a material by multiple orders of magnitude). An interface between the two techniques must somehow be able to reduce or dilute overly large amounts of volatile materials to avoid saturation of the MS.

FIG. 1 shows a prior art arrangement of a TGA linked to a MS via an interface, i.e., a capillary column of uniform diameter. The three essential components are shown: a thermobalance 1, shown as a DuPont Instruments 951 (TGA; a mass spectrometer 2, shown as a quadruple analyzer with accompanying RF generator 11; and the capillary interface 3 which couples the two devices. Operation of the furnace and the balance assemblies of the TGA (i.e., control of the sample temperature and measured sample weight) are controlled by a personal computer (PC) 12 with module interface. Volatiles from the sample heated in the TGA are pulled through the capillary via a pressure differential (i.e., reduced pressure at the MS end of the interface) and are subsequently leaked into the MS. In the MS, the incoming gas molecules are ionized and the ions (some of which have undergone fragmentation) are sorted in the quadruple analyzer. This sorting of ions is accomplished by changing the RF field between the poles of the analyzer, filtering the ions according to their mass-to-charge ratios. The entire operation of the MS (including RF generator) is controlled by a second PC 13.

E. L. Charsley, et al. in an article entitled "Thermogravimetry-mass spectrometry using a simple capillary interface", published in American Laboratory, January 1990, describes a TGA-MS system shown in FIG. 1, that comprises a thermobalance 1, a mass spectrometer 2, and an interface coupling the two apparatus. Linking the TGA equipment to a MS presents a problem that each of the two apparatus operate at different pressures.

Whereas the TGA normally operates in an atmospheric pressure environment, the MS must operate below $10^{-5}$ mbar. To reduce the pressure of the carrier and of the evolved gas prior to analysis, a flexible and inert fused silica-lined stainless steel capillary 3 is used, having an inner diameter approximately 0.3 mm, and a length ranging from 6" to 4'. The capillary has one end positioned in the thermobalance in close proximity of the sample 4, and the other 5 is connected to the second stage of a rotary pump (not shown) linked with the MS. In this manner, the gas flow to the MS is drastically reduced. The alumina probe 6 positioning the capillary 3 close to the sample 7, e.g., a polymer, has a separate resistance heater (not shown), preferably connected in series to a stainless steel sheath 8. Both ends of the capillary column are respectively secured by a Teflon connector block 9 and a seal 10.

A significant drawback of the interface linking a TGA to a MS as described in FIG. 1 lies in the difficulty of adjusting the concentration of volatiles that are introduced in the MS, a prime requirement in view of the inherent mismatch in sensitivity between the TGA and the MS.

OBJECTS OF THE INVENTION

Accordingly, it is an object of the present invention to provide an interface capable of ensuring a continuous flow of volatiles from a TGA into the capillary column.

It is another object to provide an interface that adjusts the concentration of volatiles entering an MS from a TGA.

It is yet another object of the invention to provide an interface that allows samples to be thermogravitationally analyzed in a wide range of atmospheric pressures while maintaining a continuous helium flow required for the operation of an MS.

It is still a further object to provide an interface that allows a mass spectral analysis that can be simultaneously performed on samples undergoing combustion or other oxidation processes within a TGA.

It is a more particular object to provide an interface that provides an oxidation process in an oxidizing atmosphere which may be incompatible with an MS.

It is yet a further object to provide an interface that provides mass spectral analysis at sample temperatures in excess of 450° C., which are normally beyond the upper temperature limit of the capillary feeding into an MS.

It is still another object to provide an interface that allows heating the capillary in a temperature-programmable mode to replicate the temperature profile of a TGA throughout the analysis.

It is yet a more particular object to provide an interface capable of maintaining the mass spectral integrity of thermal labile species, i.e., to prevent thermolysis of such species in an excessively hot transfer line and thusly prevent alteration of the resulting mass spectra.

SUMMARY OF THE INVENTION

The foregoing and other objects of the invention are achieved by an apparatus for performing a thermogravimetric analysis of a material under test, comprising: a thermogravimetric analyzer (TGA) for performing the gravimetric analysis at a predetermined rate of change of temperature; a mass spectrometer (MS) for providing simultaneous mass spectral analysis; a capillary column in fluid communication between the TGA and the MS for transferring effluents from the TGA into the MS; and means for controlling the temperature of the capillary column to track and replicate the temperature of the thermal profile of the TGA at the predetermined rate of change of temperature.

BRIEF DESCRIPTION OF THE DRAWINGS

The features characteristic of this invention as well as other objects and advantages thereof may best be understood by reference to the following detailed description of two preferred embodiments to be read in conjunction with the accompanying drawings, in which.

DETAILED DESCRIPTION OF THE INVENTION

Two alternative embodiments (FIGS. 3 and 4) for interfacing the mass spectrometer (HS) to the thermogravimetric analyzer TGA are herein described. Both interfaces utilize a single fused silica capillary 3 which is continuous in length, i.e., there is no termination of the capillary at a splitting area inside the transfer line. The internal diameter (ID) of the capillary can range from 0.15 mm to 0.4 mm, with a preferred ID of 0.25 mm. The length of the capillary can range from 6 inches to 4 feet, depending on the spatial configurations of the TGA and MS, but should be kept as short as possible to keep the time of transfer of volatiles from the TGA to the MS at a minimum (typically, only a maximum of a few seconds). A polymer, such as a cured polyimide, coats the fused silica phase to provide support and flexibility (a standard non-polar gas chromatography column with the appropriate ID can be cut to length and is ideal for use as a capillary.)

Figure 3:
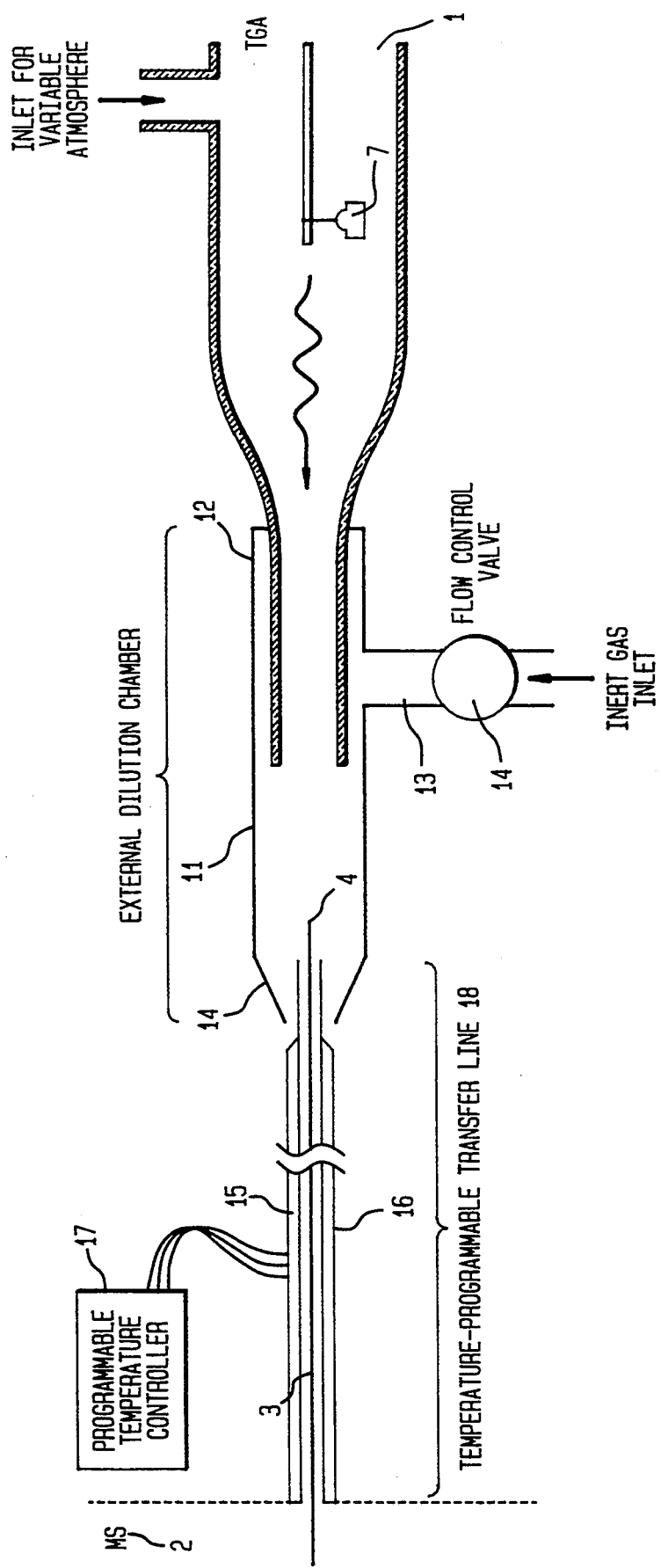
FIG. 3 shows a schematic of the same interface modified by the presence of an external dilution chamber and a temperature-programmable transfer line in accordance with a first preferred embodiment of the present invention.

In the first embodiment shown in FIG. 3, the capillary originates at the MS vacuum manifold and extends into a dilution chamber 11 which is external to both the MS transfer line and the TGA cell. As shown in FIG. 3, the dilution chamber is a glass tube approximately 3 inches in length fitted with two inlets 12 and 13 and one outlet 14 for gases. Inlet 12 slides over the outlet of the TGA furnace tube and allows the volatiles from the TGA to be swept into the dilution chamber. Inlet 13 allows inert gas such as helium or argon (required for operation of the MS) to be introduced into the dilution chamber. A standard needle valve can be used to control the flow of the inert gas into the chamber.

The internal diameter of the dilution chamber (approximately ⅜ inches) is intermediate in size between that of the TGA furnace tube and the capillary attached to the MS. This serves to help channel the flow of volatiles form the TGA into the capillary.

A second function of the dilution chamber is to allow for adjusting the concentration of volatiles that are introduced into the MS. This is often necessary because there is an inherent mismatch in sensitivity between the TGA and the MS (MS being much more sensitive). The degree of adjustment required is sample dependent; extremely volatile samples require higher dilution (i.e., higher inert gas flow from inlet 13) to avoid saturation of the MS detector. The flow rate of the diluting gas is readily adjustable via flow controller 14, allowing the analyst to instantly compensate for mismatches in sensitivity between the TGA and MS detectors.

A third function of the external dilution chamber is that it allows samples to be thermogravimetrically analyzed in a wide variety of atmospheres while maintaining the inert gas flow required for operation of the MS. This is essential if mass spectral analysis is to be simultaneously performed on samples undergoing combustion or other oxidative reactions in the TGA. These types of oxidative reactions require an oxidizing atmosphere, such as air or oxygen, which are incompatible with the mass spectrometer.

Figure 1:
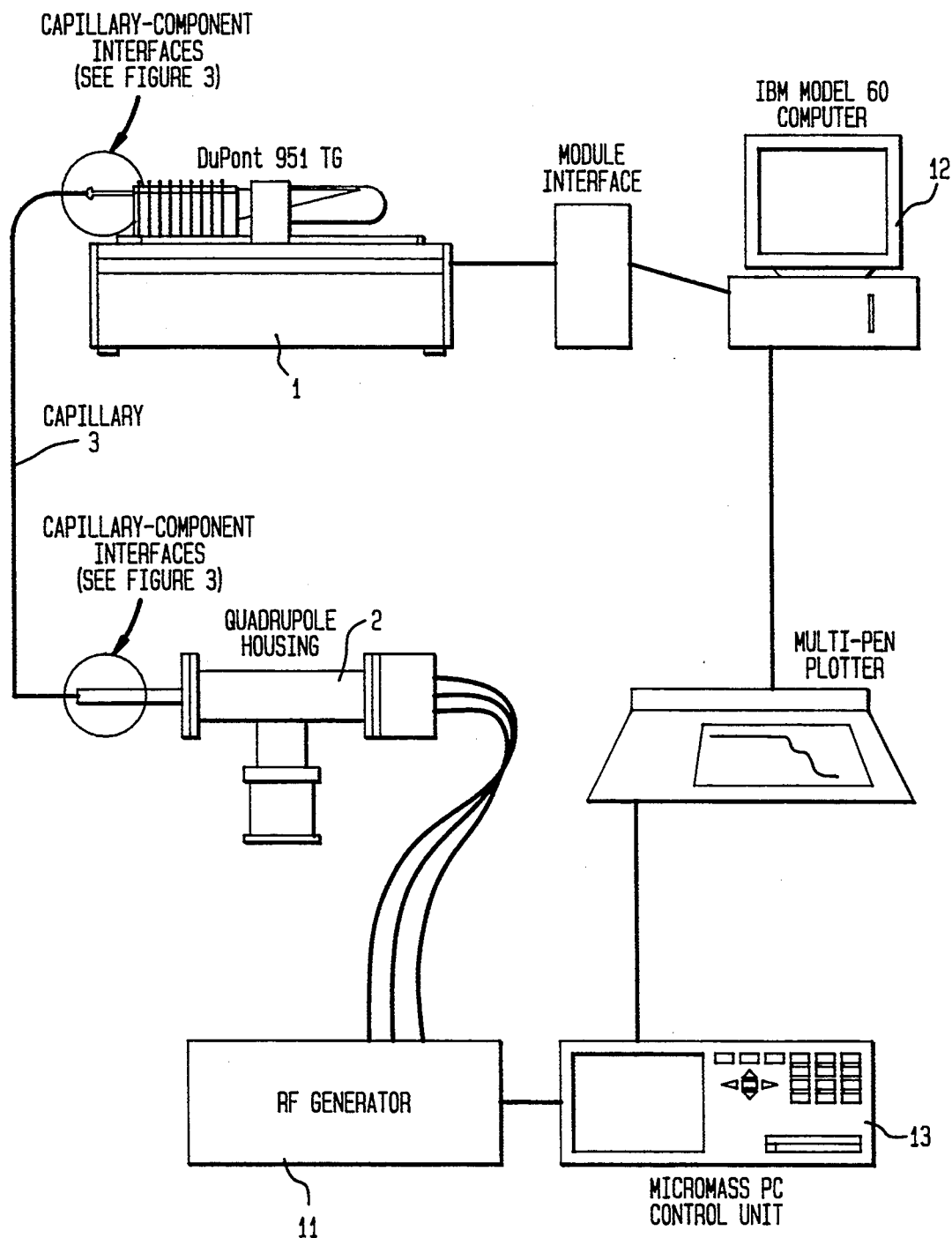
FIG. 1 shows a prior art arrangement of a TGA linked to a MS via an interface, i.e., a capillary column of uniform diameter.
Figure 2:
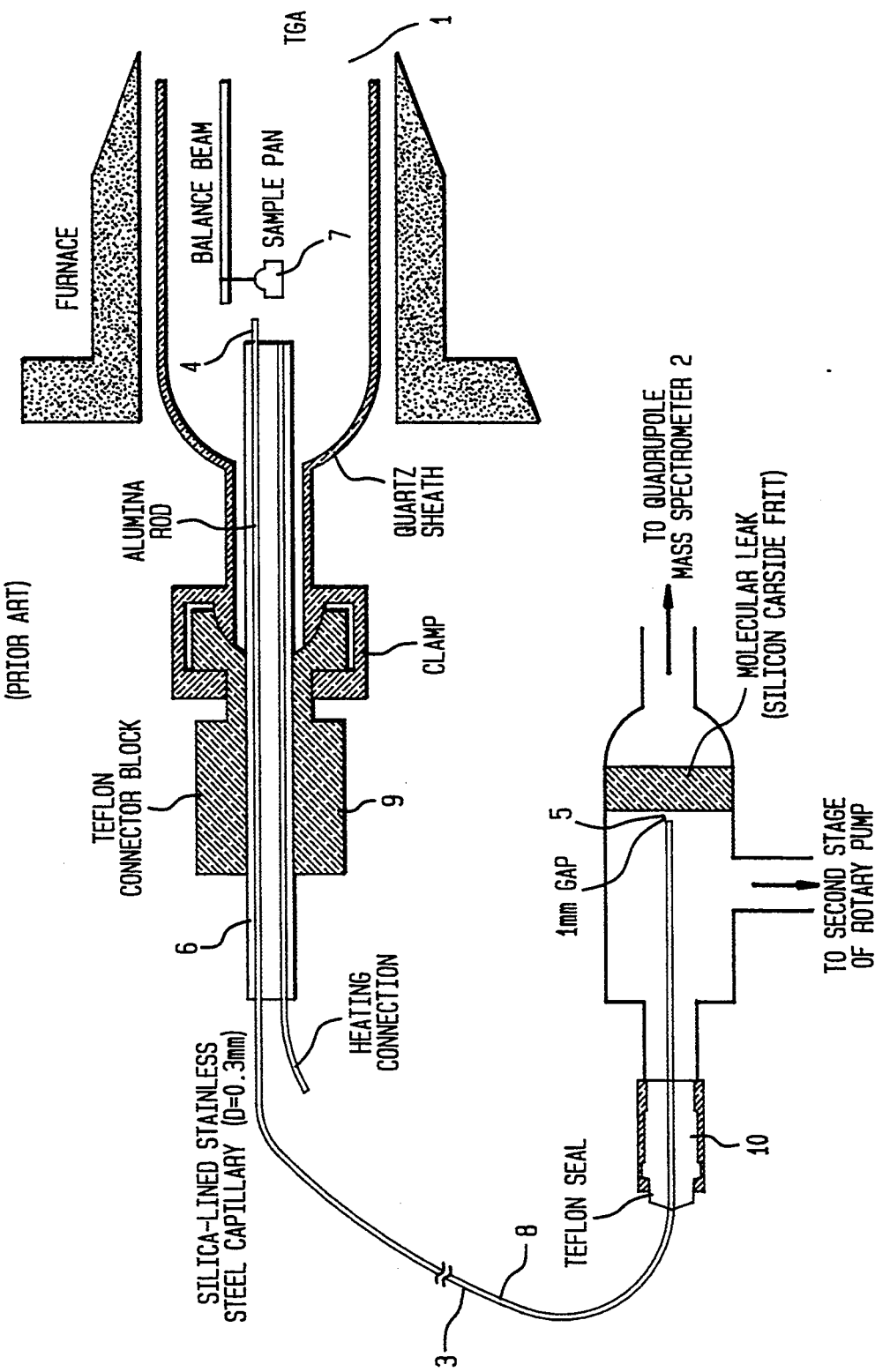
FIG. 2 shows a schematic of the same prior art interface with pertinent specifics of the interface enlarged.

Another function of the dilution chamber is that it allows mass spectral analysis at sample temperatures above the thermal degradation temperature of the capillary. The TGA furnace is capable of heating samples to 1200° C., but the capillary which extends into the TGA (4 in FIG. 2) will begin to degrade and outgas siloxanes beginning at a much lower temperature (approximately 450° C.). Termination of the capillary in the dilution chamber rather than the furnace tube thus substantially extends the upper limit for the temperature range of the analysis (more than doubling the approximate 450° C. upper limit of the prior art configuration to 1200° C.).

The fragile capillary is encased from the outlet of the MS to the inlet of the dilution chamber in 1/16 inch stainless steel tubing 15, which is subsequently encased in a temperature-programmable sheath heater 16. The temperature of the sheath heater is controlled by a microprocessor based programmable temperature controller 17 which has the ability to perform multiple ramp and soak profiles. The capillary/transfer line 18 temperature can thus be made to replicate the temperature profile of the TGA throughout the analysis. This feature is critical for maintaining the mass spectral integrity of thermal labile species (thermolysis of such species in an excessively hot transfer line can significantly alter the resulting mass spectra.) Prior art versions of TGA-MS interfaces have the transfer line maintained at a constant temperature (typically 200° C. to 300° C.), and thus risk degradation of thermally labile compounds in the transfer line prior to mass spectral analysis.

Figure 4:
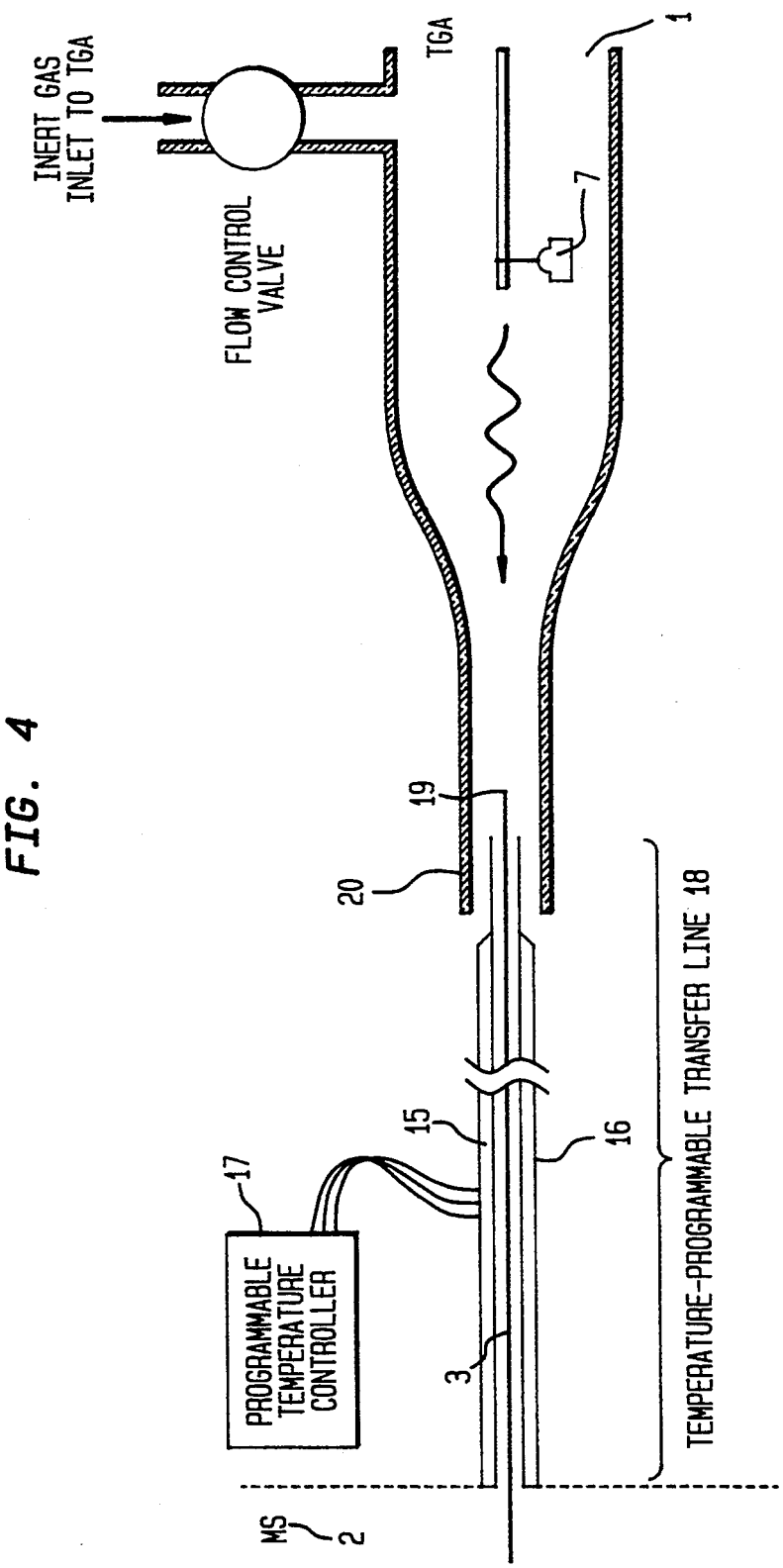
FIG. 4 shows a second preferred embodiment of the present invention, wherein the interface is provided with a direct capillary insertion having a temperature-programmable transfer line.

Referring now to a second embodiment in FIG. 4, a temperature-programmable interface 18 is achieved by bypassing the dilution chamber and feeding the capillary tip directly into the TGA furnace tube. The capillary terminates 19 within close proximity of the TGA sample pan 7 and volatiles are pulled through the capillary into the MS source. The capillary 3 is preferably protected by a 1/16 inch stainless steel 15. A sheath heater 16 surrounds the stainless steel and extends from the mass spectrometer inlet to the outlet of the TGA furnace tube 20. Once again, a micro-processor based programmable temperature controller 17 with multiple ramp and soak capability is used to control the temperature of the programmable transfer line 18.

This direct insertion design allows for extremely efficient transfer of volatile species directly into the MS from the TGA. However, there are more limitations on analysis conditions: without the external dilution chamber 11, the inert atmosphere requirement for operation of the MS implies that samples can only be analyzed in the TGA in an inert environment (combustion and other oxidation reaction studies cannot be done). Also, because the capillary is inserted directly into the TGA furnace tube, the upper temperature limit for analysis becomes that of the thermal stability of the capillary itself, approximately 450° C.

An additional advantage of the external dilution chamber over direct capillary insertion is a significantly reduced purge time: direct insertion requires that the TGA be purged with inert gas for 30 minutes after sample introduction to bring oxygen and water down to levels acceptable to the MS. The required purge time with the external dilution chamber is only 3 minutes.

Both embodiments, i.e., the external dilution chamber with temperature-programmable transfer line (FIG. 3) and the direct capillary insertion with temperature-programmable transfer line (FIG. 4) allow thermally labile samples to be thermogravimetrically analyzed at ambient pressure with simultaneous detection at high sensitivity by MS.

While the invention has been particularly shown and described with reference to two preferred embodiments thereof, it will be understood by those skilled in the art that the foregoing and other changes in the form and details may be made therein without departing from the scope and spirit of the invention.

What is claimed is:

1. An apparatus for performing thermogravimetric analysis of a material under test, comprising:
   a thermogravimetric analyzer (TGA) for performing gravimetric analysis at a predetermined rate of change of temperature;
   a mass spectrometer (MS) for providing simultaneous mass spectral analysis;
   a capillary column in fluid communication linking the TGA to the MS, for transferring effluents from the TGA into the MS; and
   means for controlling the temperature of the capillary column to track and replicate the temperature of the TGA at the predetermined rate of change of temperature.

2. The apparatus as recited in claim 1 further comprising a dilution chamber provided with two ends, one of said ends is attached to the TGA and the second is connected to an end of said capillary column.

3. The apparatus as recited in claim 1, wherein said TGA is provided with a furnace tube, said tube being connected to the end of said chamber.

4. The apparatus as recited in claim 2, wherein said dilution chamber is provided with at least two inlets and one outlet, the first of said two inlets is connected to the TGA for allowing volatiles from the TGA to be swept into the dilution chamber and for adjusting the concentration of said volatiles to be introduced into said MS, the second of said inlets is connected to a source of gases to be introduced in said chamber, and wherein the outlet of said chamber provides a connection to the end of the capillary column.

5. The apparatus as recited in claim 4, wherein said gas is an inert gas.

6. The apparatus as recited in claim 4, wherein said second inlet is controlled by a valve that controls the flow of said gas into said dilution chamber.

7. The apparatus as recited in claim 3, wherein the diameter of said chamber is intermediate in size to the diameter of said TGA furnace tube and to the diameter of said capillary column.

8. The apparatus as recited in claim 3, wherein said furnace heats the material under test to 1200° C.

9. The apparatus as recited in claim 2, wherein said dilution chamber extends the temperature range by approximately 450° C. above a temperature where thermal degradation in said capillary column occurs.

10. An apparatus for performing thermogravimetric analysis of a material under test, comprising:
 a thermogravimetric analyzer (TGA) for performing gravimetric analysis at a predetermined rate of change of temperature;
 a mass spectrometer (MS) for providing simultaneous mass spectral analysis;
 a capillary column in fluid communication linking the TGA to the MS, for transferring effluents from the TGA into the MS; and
 a dilution chamber intermediate to the capillary column and the TGA, for allowing volatiles from the TGA to be swept into the dilution chamber, for adjusting the concentration of said volatiles to be introduced into the MS, for allowing the material to be tested to be thermogravimetrically analyzed under plural atmospheres, and for allowing mass spectral analysis at a temperature above thermal degradation of the capillary column.

11. An apparatus for performing thermogravimetric analysis of a material under test, comprising:
 a thermogravimetric analyzer (TGA) provided with a furnace tube, for performing gravimetric analysis at a predetermined rate of change of temperature;
 a mass spectrometer (MS) for providing simultaneous mass spectral analysis;
 interface means linking the TGA to the MS, for transferring effluents from the TGA into the MS extending from the MS to the TGS near the material to be tested; and
 programmable heating means surrounding the interface means extending from the MS to near the TGA furnace tube for controlling the temperature within the interface means.

12. The apparatus for performing thermogravimetric analysis of a material under test as recited in claim 11, wherein said interface means is a capillary column made of glass surrounded by a protective layer of stainless steel.

13. The apparatus for performing thermogravimetric analysis of a material under test as recited in claim 12, wherein the heating means is a sheath heater surrounding the protective layer.

14. The apparatus for performing thermogravimetric analysis of a material under test as recited in claim 11, wherein the material to be tested in the TGA is placed in an inert environment.

15. The apparatus for performing thermogravimetric analysis of a material under test as recited in claim 11, wherein an upper temperature limit for the material to be tested is limited by the thermal stability of the interface means.

16. The apparatus for performing thermogravimetric analysis of a material under test as recited in claim 15, wherein the upper temperature limit is approximately 450° C.

* * * * *